United States Patent [19]

Miura

[11] Patent Number: 5,092,941

[45] Date of Patent: Mar. 3, 1992

[54] METHOD FOR IMPARTING SHAPES TO SHAPE MEMORY ALLOY WIRES

[75] Inventor: Fujio Miura, Sakae, Japan

[73] Assignee: GAC International, Inc.

[21] Appl. No.: 432,792

[22] Filed: Nov. 6, 1989

[30] Foreign Application Priority Data

Feb. 10, 1989 [JP] Japan .................................. 1-29939

[51] Int. Cl.⁵ .............................................. C22F 1/00
[52] U.S. Cl. .............................. 148/11.5 N; 148/402; 148/426; 433/20
[58] Field of Search ....................... 433/18, 20, 21, 24; 148/11.5 N, 402, 426

[56] References Cited

FOREIGN PATENT DOCUMENTS 58-50950  3/1983  Japan .

Primary Examiner—R. Dean
Assistant Examiner—Robert R. Koehler
Attorney, Agent, or Firm—Kenyon & Kenyon

[57] ABSTRACT

A method of imparting a particular shape to a wire made of a shape memory alloy, such as a Ni-Ti alloy, which includes the steps of bending the wire inside a tubular body into the particular shape; heating the wire within the tubular body to a temperature sufficient to cause the wire to retain the particular shape; and removing the wire from the tubular body. The tubular body is made of a deformable metal, such as stainless steel or nickel-chrome alloy tubing, and includes a slit therethrough extending in its axial direction. The slit is provided to facilitate bending the tubular body and removing the wire from the tubular body.

24 Claims, 3 Drawing Sheets

METHOD FOR IMPARTING SHAPES TO SHAPE MEMORY ALLOY WIRES

FIELD OF THE INVENTION

The present invention relates to alloy wires exhibiting shape memory properties and, in particular, to methods and apparatus for imparting predetermined shapes to such wires.

BACKGROUND OF THE INVENTION

In conventional orthodontic treatment, orthodontic brackets are mounted to the surfaces of a patient's teeth, and an arch-shaped orthodontic wire is fastened to the brackets with ligature wire. The arch-shaped wire imparts forces to the teeth, which are created by the bending and resultant tension within the wire. The wire is shaped so that the forces exerted by the wire move the teeth, so as to correct the malocclusion of the patient's dental arch.

Recently, alloy wires exhibiting shape memory properties, such as nickel-titanium (Ni-Ti) alloy wires, have been used to make orthodontic wires. Alloy wires possessing shape memory properties are readily amenable to change in shape at low temperatures, but can be reformed to their original configurations when heated to suitable transition temperatures. The alloy wires exhibiting shape memory properties, such as the Ni-Ti alloy wires, are frequently referred to as shape memory alloy wires Some shape memory alloy wires, like the Ni-Ti alloy wires, exhibit excellent superelastic and springback properties. Superelasticity occurs when the stress value remains substantially constant up to a certain point of wire deformation, and when the wire deformation rebounds, the stress value again remains substantially constant. Therefore, when a Ni-Ti archwire, for example, is subjected to a load to create a deflection, the load remains substantially constant throughout a given superelastic zone of deflection of the wire. Moreover, because such shape memory wires possess excellent springback properties, they can be deflected to greater degrees than other types of wires, without causing permanent deformation of the wire.

Orthodontic shape memory alloy wires are formed so as to retain particular shapes. The shape of an orthodontic wire is determined depending upon the malocclusion of a patient's teeth, in order to exert forces and thus move the teeth to correct the malocclusion. When a shape memory alloy wire is mounted to the orthodontic brackets on a patient's teeth, the wire is deflected and tends to springback to the particular shape previously imparted to the wire, thus applying a force and in turn shifting the teeth. While such use has occurred, it has failed to provide a method or apparatus for shaping wires made of shape memory alloys so as to retain a particular shape in a manner that is simple, accurate, and relatively inexpensive to perform.

One method of imparting shapes to shape memory alloy wires is shown in Japanese patent Early Disclosure 58-50950 (1983), wherein restraining channels are formed into a mold or pattern made of gypsum or glass. Each restraining channel is made in the shape that a wire should take in order to correct a particular patient's malocclusion. The wire is then fitted into the restraining channel and heated to a temperature sufficient to cause the wire to retain the shape of the channel. Therefore, when the shape memory wire is deflected within its elastic range, it will springback into the particular shape imparted by the channel.

One problem with the gypsum or glass molds is that they are relatively time consuming and therefore expensive to build. Each mold or pattern must be formed so that its restraining channel imparts the unique shape to the orthodontic wire required to meet the needs of an individual patient. Because one patient's malocclusion is usually different than another's, it is usually necessary to prepare an individual mold or pattern for each patient. Therefore, the gypsum or glass molds are generally not economically feasible because each mold usually can only be used for one patient. Moreover, it is frequently necessary to impart three-dimensional shapes or, that is, shapes formed in more than one plane to orthodontic wires. With gypsum or glass molds, however, it is usually difficult to form the molds to impart the three-dimensional shapes, thus making the use of molds even more time consuming and expensive.

Under another known method of imparting shapes to shape memory alloy wires, each end of a shape memory alloy wire is gripped with a pair of electric pliers. The pliers are typically coupled to a constant-current generating apparatus. Electrode plates mounted within the pliers pass electric current through the wire in order to heat the wire. While heating the wire, the operator bends the wire into a desired shape by manipulating the pliers. The operator then tries to hold the wire in place until the wire reaches a temperature sufficient to cause the wire to retain the new shape. One problem with this method is that it is usually difficult for the operator to maintain the wire in the same shape throughout the heating process. As a result, the exact shape required is frequently not accurately imparted to the shape memory alloy wire.

Therefore, it is an object of the present invention to provide a method and apparatus for imparting shape to shape memory alloy wires that overcome the problems of known methods and apparatus.

SUMMARY OF THE INVENTION

The present invention is directed to a method of forming a wire made of a shape memory alloy so as to retain a predetermined shape. The method comprises the following steps: bending a wire made of a shape memory alloy inside a tubular body into a predetermined shape; heating the wire within the tubular body to a temperature sufficient to cause the wire to retain the predetermined shape; and removing the wire from the tubular body.

In one embodiment of the present invention, the wire is made of a nickel-titanium alloy exhibiting superelastic properties, and is heated to a temperature of about 500° C. Also, the predetermined shape to be retained by the wire is determined to correct a patient's malocclusion. The tubular body can be initially deformed into the predetermined shape, and the wire can then be inserted into the tubular body. Likewise, the wire can initially be inserted into the tubular body, and the tubular body can then be deformed into the predetermined shape. The cross-sectional shape of the tubular body is selected to substantially correspond to the cross-sectional shape of the wire. Preferably, the tubular body and wire are heated by passing electric current through the tubular body and the wire, although the electric current may be passed through either the tubular body or wire.

In another embodiment of the present invention, a temperature sensitive coating is applied to the tubular body. The temperature sensitive coating is selected so that it discolors when the tubular body reaches a temperature sufficient to cause the wire to retain the predetermined shape. The tubular body is preferably made of a stainless steel tubing or a nickel-chrome alloy tubing.

The present invention is also directed to an apparatus for forming a wire made of a shape memory alloy so as to retain a predetermined shape. The apparatus comprises a tubular body arranged to receive the wire. The tubular body is made of a deformable metal and is adapted to be deformed into a predetermined shape, and heated to a temperature sufficient to cause the wire to retain the predetermined shape of the tubular body.

In one embodiment of the apparatus of the present invention, the tubular body includes a slit therethrough extending in its axial direction. The slit is provided to facilitate bending the tubular body and removing the wire from the tubular body. The tubular body is made of a material exhibiting substantial electrical resistivity, in order to generate sufficient heat by passing electric current therethrough, to cause the wire to retain the predetermined shape of the tubular body.

The tubular body can thus be made of stainless steel tubing, or a nickel-chrome alloy tubing. The cross-sectional shape of the tubular body is selected to substantially mate with the cross-sectional shape of the orthodontic wire to be inserted therein.

The present invention is also directed to a method of shaping an orthodontic wire made of a shape memory alloy, so as to retain a predetermined shape. The method comprises the following steps: deforming the wire within a tubular body into the predetermined shape; heating the wire within the tubular body to a temperature sufficient to cause the wire to retain the predetermined shape; and cooling the wire and removing the wire from the tubular body.

In one embodiment of the method of the present invention, prior to removing the wire from the tubular body, the tubular body is deformed sufficiently within the superelastic range of the wire to facilitate removing the wire from the tubular body, while retaining the predetermined shape of the wire. The tubular body can be initially deformed into the predetermined shape, and the wire then inserted into the tubular body. Likewise, the wire can be initially inserted into the tubular body, and the tubular body can then be deformed into the predetermined shape. The wire to be shaped is preferably made of a nickel-titanium alloy exhibiting superelastic properties, and is heated to about 500° C. Preferably, the wire is heated by generating electric current through the wire, although the wire can also be heated by generating electric current through the tubular body. The tubular body is preferably made of a metal exhibiting substantial electrical resistivity, such as a stainless steel or nickel-chrome alloy, in order to generate sufficient heat by passing electric current therethrough to heat the wire to retain the predetermined shape One advantage of the present invention, is that the tubular body can be accurately deformed into the shape desired to be retained by the shape memory alloy wire, and thus employed to accurately impart that shape to the wire. As a result, the orthodontic wire can be deformed accurately and relatively quickly at a substantial cost savings to the patient.

Another advantage of the present invention is that the tubular body can be reused to shape more than one orthodontic wire. Yet another advantage of the present invention, is that prior to removing the orthodontic wire from the tubular body, the tubular body can be deformed again into a shape within the superelastic range of the wire, that will facilitate the removal of the wire from the tubular body, while retaining the predetermined shape of the wire. As can be seen, accurate and relatively complicated shapes can be imparted to orthodontic wires by employing the apparatus and method of the present invention.

Other advantages of the present invention will become apparent in view of the following detailed description and drawings taken in connection therewith.

DETAILED DESCRIPTION

Figure 1:
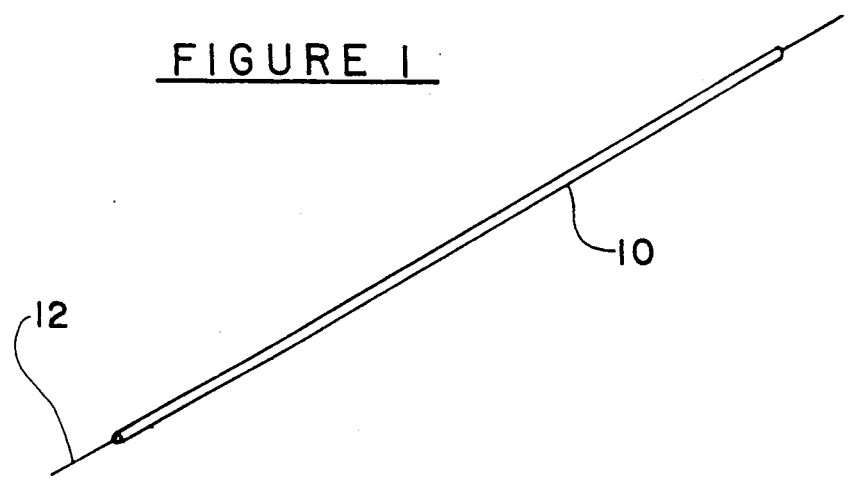
FIG. 1 is a perspective view of an orthodontic wire inserted within a tubular body embodying the present invention.

In FIG. 1, a metal tubular body embodying the present invention is indicated generally by the reference numeral 10. The tubular body 10 is made of a thin, deformable metal or foil, such as stainless steel tubing or a nickel-chrome alloy tubing. The tubular body 10 initially has a linear shape, and is shown fitted over an orthodontic wire 12, which is made of a shape memory alloy wire, such as a Ni-Ti alloy wire, exhibiting superelastic and springback properties.

Figure 2:
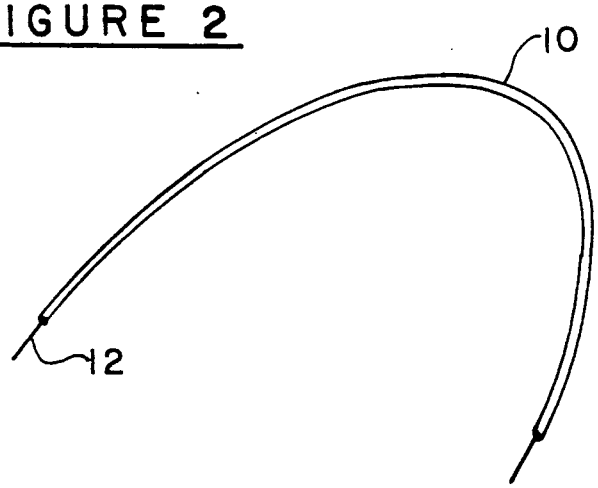
FIG. 2 is a perspective view of the orthodontic wire and tubular body of FIG. 1, shown deformed in accordance with the method of the present invention.
Figure 4A:
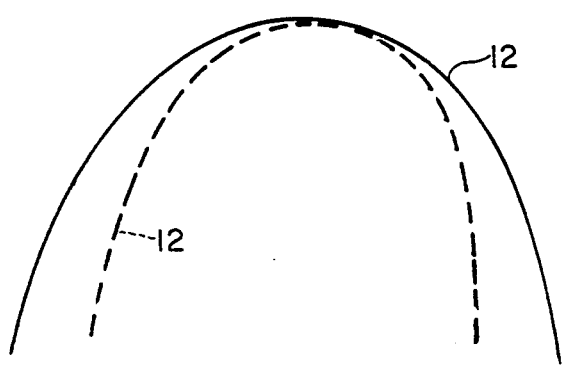
FIGS. 4A-4D are schematic views illustrating various shapes that can be imparted to the orthodontic wires in accordance with the present invention.
Figure 4B:
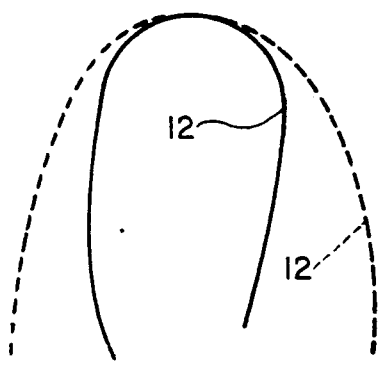
Figure 4C:
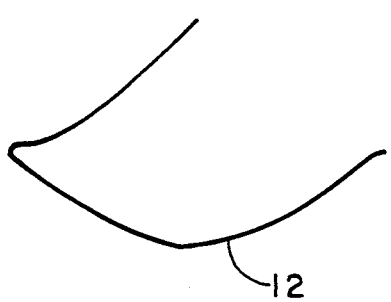
Figure 4D:
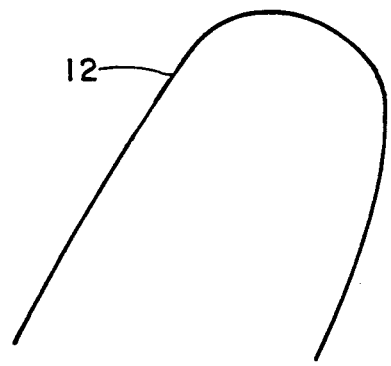

In FIG. 2, the tubular body 10 is shown deformed into a predetermined shape, in order to cause the orthodontic wire 12 to retain the shape, in accordance with the method of the present invention. The tubular body 10 is deformed by any of several known manual bending processes, machine bending processes, or such other bending processes known to those skilled in the art. The shape imparted to the tubular body 10 is determined depending upon the particular needs of the patient using the orthodontic wire 12. After the orthodontic wire 12 is deformed within the tubular body 10, both the wire and tubular body are heated to a temperature sufficient to cause the wire 12 to retain the deformed shape of the tubular body 10. As a result, the required shape, as formed by the tubular body 10, is imparted to the orthodontic wire 12. It should be noted that the tubular body 10 can be deformed with the orthodontic wire 12 inserted therein, or it can be deformed without the wire 12, and the wire 12 can then be inserted into the tubular body 10 after it is deformed.

Figure 3A:
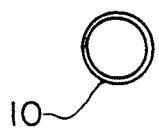
FIGS. 3A-3D illustrate cross-sectional views of differently shaped tubular bodies embodying the present invention.
Figure 3B:
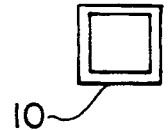
Figure 3C:
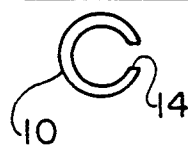
Figure 3D:
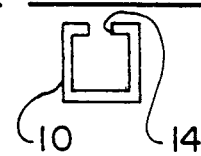

The cross-sectional shape of the tubular body 10 is selected to substantially correspond to or mate with the cross-sectional shape of the orthodontic wire 12, so that the orthodontic wire 12 can accurately retain the shape imparted to the tubular body 10. Therefore, the tubular body 10 can take many different cross-sectional shapes depending upon the shape of the orthodontic wire 12 that is used. For example, the cross-section of the tubular body 10 can be circular or square shaped, as shown in FIGS. 3A and 3B, respectively. Likewise, the cross-section of the tubular body 10 can take the form of a round or square shape, and can further define a linear slit 14 extending along its entire length, as shown in FIGS. 3C and 3D, respectively. The slit 14 is provided to facilitate bending the tubular body and facilitate removing the wire 12 from the tubular body 10 after the wire is deformed. As can be seen, so long as the orthodontic wire 12 is confined within the tubular body 10, the wire 12 and tubular body 10 can take the form of various cross-sectional shapes.

To heat the tubular body 10 and orthodontic wire 12, several heating methods known to those skilled in the art may be used. Preferably, an electric heating apparatus (not shown) employing a light, constant-current generating device is used. Such devices typically include a pair of electric pliers for gripping each end of the wire 12 or the tubular body 10 to generate electric current therethrough. However, although the electric pliers are preferred, a conventional heating method using a heating furnace, or other known method of heating may equally be used. In using electric pliers, the electric current is passed through the orthodontic wire 12 itself or, alternatively, the electric current is passed through the tubular body 10 which has the orthodontic wire 12 inserted therein. The wire 12 and tubular body 10 are then heated to a temperature sufficient to cause the orthodontic wire 12 to retain the shape of the tubular body 10 when the wire is removed from the tubular body.

In the embodiment of the present invention shown in FIG. 1, the orthodontic wire 12 is preferably heated by passing electric current through the metal tubular body 10, with a constant-current generating apparatus. A stainless tube or nickel-chrome alloy tube, which exhibits substantial electrical resistivity in order to generate enough heat to sufficiently heat the orthodontic wire 12 when current is generated therethrough, is preferably used to make the tubular body 10. The tubular body 10 is first deformed into the shape that should be imparted to the wire 12 to treat a particular patient's malocclusion, and the orthodontic wire 12 is then inserted inside the tubular body 10. Each end of the deformed tubular body 10 is then gripped with the electric pliers of the constant-current generating apparatus. Electric current is then generated through the tubular body 10 until the tubular body and, therefore, the orthodontic wire 12 reach a temperature of about 500° C. The heat generated by the electric current in turn causes the orthodontic wire 12 to retain the shape of the tubular body 10. The orthodontic wire 12 is then cooled and withdrawn from the tubular body 10. The shape of the tubular body 10 is thus accurately retained by the orthodontic wire 12, which can then be employed to accurately straighten the patient's teeth for which the predetermined shape of the orthodontic wire was designed. It should be noted that although the heating temperature is preferably about 500° C. when the orthodontic wire 12 made of a Ni-Ti alloy, the exact temperature and time of heating may be varied depending upon the composition of the wire 12 and the tubular body 10, and depending upon their respective sizes and shapes.

One advantage of the present invention, is that after the orthodontic wire 12 is heated to retain the shape of the tubular body 10, the tubular body 10 can then be deformed again into a shape that will facilitate withdrawal of the wire 12 therefrom. It should be noted, however, that the tubular body 10 should be deformed only within the elastic range of the wire 12 in order to maintain the desired shape of the wire. Frequently, however, because of the elastic properties of the shape memory alloy wire used to make the orthodontic wire 12, after the wire 12 is cooled, the tubular body 10 can be deformed back into a near linear shape in order to facilitate removing the wire 12 therefrom, and the wire 12 will still retain the original deformed shape of the tubular body 10.

As shown in FIG. 4, by employing the method and apparatus of the present invention, a variety of shapes can be imparted to orthodontic wires made of Ni-Ti, or other types of shape memory alloys. For example, a linear wire 12 may be formed into a standard arch-shape as shown by either the dotted line in FIG. 4A or the dotted line in FIG. 4B. Likewise, an orthodontic wire 12 that has already been formed into a standard arch-shape, may be formed into a wide arch-shape, as shown by the solid line in FIG. 4A, or into a narrow arch-shape, as shown by the solid line in FIG. 4B. Similarly, by employing the method and apparatus of the present invention, an orthodontic wire 12 having a linear shape or an arch form already made, can be formed into a three-dimensional shape or, that is, a shape formed in more than one plane, as shown for example in FIG. 4C, or can be formed into a special shape as shown in FIG. 4D.

Figure 5:
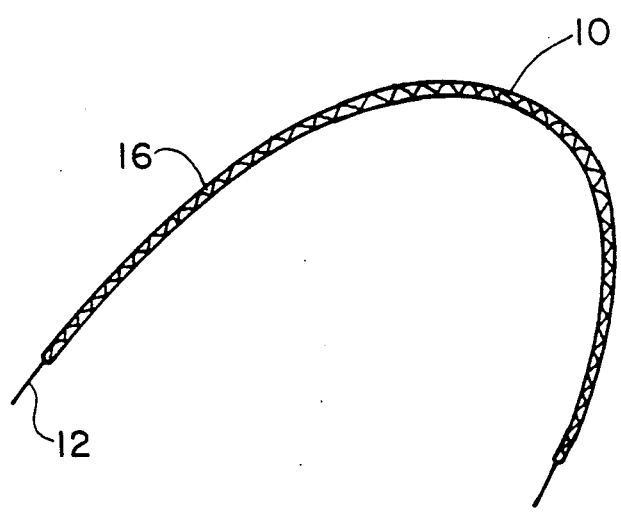
FIG. 5 is a perspective view of another embodiment of an orthodontic wire inserted within a tubular body embodying the present invention.

In FIG. 5, another embodiment of the present invention is shown, wherein a temperature sensing paste or coating 16, known to those skilled in the art, is applied to the outer surface of the tubular body 10. The temperature sensing paste 16 is applied in order to determine when the temperature of the tubular body 10 reaches a level sufficient for the wire 12 to retain the shape of the tubular body 10. In the embodiment described above, the temperature sensing paste would be selected so that the paste discolors when heated to about 500° C. Therefore, one advantage of the temperature sensing paste 16, is that an operator can accurately determine when to stop generating electric current through the tubular body 10 and orthodontic wire 12. The constant-current generating apparatus may therefore include a relay to control the flow of electric current so that when the desired temperature is reached, the relay may be turned off in order to permit the wire 12 to cool. Another advantage of the temperature sensing paste 16, is that it permits an operator to detect variations in the electrical resistivity between different points or locations on the tubular body 10, depending upon the variations in the color change of the temperature sensing paste 16.

One advantage of the present invention is that each metal tubular body 10 can be deformed repeatedly for use with different patients. Therefore, unlike other known methods, such as those using patterns or molds, because the tubular body 10 can be reused, the present invention can provide significant cost savings to patients.

It should also be noted that because the orthodontic wire 12 can usually be easily withdrawn from the metal tubular body 10, relatively complicated shapes can be imparted to the orthodontic wire. The method and apparatus of the present invention may also be easily employed to impart a particular shape to only a part of an orthodontic wire 12, rather than to the whole wire.

It should also be noted that while the method and apparatus of the invention are particularly suitable for shaping orthodontic wires, the present invention is equally applicable to other fields. For example, the present invention can be used to shape wires made of shape memory alloys that will retain shapes necessary to shape or support garments.

What is claimed is:

1. A method of forming a wire made of a shape memory alloy so as to retain a predetermined shape, said method comprising the following steps:
    bending a wire made of a shape memory alloy inside a tubular body into a predetermined shape;
    heating said wire within said tubular body to a temperature sufficient to cause said wire to retain said predetermined shape; and
    cooling said wire and removing said wire from said tubular body.

2. A method as defined in claim 1, wherein said wire is made of a nickel-titanium alloy exhibiting superelastic properties.

3. A method as defined in claim 2, wherein said wire is heated to a temperature of about 500° C.

4. A method as defined in claim 1, wherein said predetermined shape retained by said wire is determined to correct a patient's malocclusion 5. A method as defined in claim 4, wherein said tubular body is initially deformed into said predetermined shape and said wire is then inserted into said tubular body.

6. A method as defined in claim 4, wherein said wire is inserted into said tubular body and said tubular body is then deformed into said predetermined shape.

7. A method as defined in claim 4, wherein the cross-sectional shape of said tubular body is selected to substantially correspond to the cross-sectional shape of said wire.

8. A method as defined in claim 4, wherein said tubular body and said wire are heated by passing electric current through said tubular body.

9. A method as defined in claim 8, wherein said wire is made of a nickel-titanium alloy exhibiting superelastic properties, and said tubular body and said wire are heated to about 500° C.

10. A method as defined in claim 4, wherein said wire is heated by passing electric current therethrough.

11. A method as defined in claim 10, wherein said wire is made of a nickel-titanium alloy possessing superelastic properties, and is heated to about 500° C.

12. A method as defined in claim 1, said method further comprising the following step:
    applying a temperature sensitive coating to said tubular body, said coating being selected so that it discolors when said tubular body reaches a temperature sufficient to cause said wire to retain said predetermined shape.

13. A method as defined in claim 1, wherein said tubular body is made of stainless steel tubing.

14. A method as defined in claim 1, wherein said tubular body is made of a nickel-chrome alloy tubing.

15. A method of shaping an orthodontic wire made of a shape memory alloy, so as to retain a predetermined shape, said method comprising the following steps:
    deforming the wire within a tubular body into the predetermined shape;
    heating the wire within the tubular body to a temperature sufficient to cause the wire to retain the predetermined shape; and
    cooling the wire and removing the wire from the tubular body.

16. A method as defined in claim 15, wherein prior to removing the wire from the tubular body, the tubular body is deformed within the superelastic range of the wire, to facilitate removing the wire from the tubular body while retaining the predetermined shape of the wire.

17. A method as defined in claim 15, wherein the tubular body is initially deformed into the predetermined shape and the wire is then inserted into the tubular body.

18. A method as defined in claim 15, wherein the wire is initially inserted into the tubular body, and the tubular body is then deformed into the predetermined shape.

19. A method as defined in claim 15, wherein the wire is heated to about 500° C.

20. A method as defined in claim 15, wherein the wire is made of a nickel-titanium alloy exhibiting superelastic properties.

21. A method as defined in claim 15, wherein the wire is heated by generating electric current through the wire.

22. A method as defined in claim 15, wherein the wire is heated by generating electric current through the tubular body.

23. A method as defined in claim 22, wherein the tubular body is made of a metal exhibiting substantial electrical resistivity to generate sufficient heat by passing electric current therethrough, in order to cause the wire to retain the predetermined shape.

24. A method as defined in claim 23, wherein the tubular body is made of a nickel-chrome alloy or stainless steel.

* * * * *